United States Patent
Luo et al.

(10) Patent No.: US 9,917,254 B2
(45) Date of Patent: Mar. 13, 2018

(54) ENCAPSULATION PACKAGE, DISPLAY DEVICE AND PACKAGING METHOD

(71) Applicant: BOE TECHNOLOGY GROUP CO., LTD., Beijing (CN)

(72) Inventors: Chengyuan Luo, Beijing (CN); Donghui Yu, Beijing (CN); Wenfeng Song, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 0 days.

(21) Appl. No.: 15/248,131

(22) Filed: Aug. 26, 2016

(65) Prior Publication Data

US 2017/0213976 A1 Jul. 27, 2017

(30) Foreign Application Priority Data

Jan. 26, 2016 (CN) .......................... 2016 1 0052797

(51) Int. Cl.
*H01L 51/00* (2006.01)
*G01N 21/81* (2006.01)
(Continued)

(52) U.S. Cl.
CPC ......... *H01L 51/0031* (2013.01); *G01N 21/81* (2013.01); *H01L 51/5246* (2013.01); *H01L 51/5259* (2013.01); *H01L 51/56* (2013.01); *G01N 31/222* (2013.01); *H01L 2251/568* (2013.01)

(58) Field of Classification Search
CPC . H01L 51/0031; H01L 51/5246; H01L 51/56; H01L 51/5259; H01L 51/003; G01N 21/81
See application file for complete search history.

(56) References Cited

U.S. PATENT DOCUMENTS 9,391,293 B2 * 7/2016 Cho ......................... C09J 11/00
2010/0001639 A1 1/2010 Kim et al.
2015/0362449 A1 12/2015 Suzuki

FOREIGN PATENT DOCUMENTS

CN 101615624 A 12/2009
CN 101626029 A 1/2010
(Continued)

OTHER PUBLICATIONS

Shih_Hsun Lin et al., "Synthesis of ultraviolet curable encapsulating adhesives and their package applications for organic optoelectronic devices", Solid State Sciences vol. 13, Elsevier, 2011, pp. 1990-1895.*

(Continued)

*Primary Examiner* — William Coleman
(74) *Attorney, Agent, or Firm* — Dilworth & Barrese, LLP.; Michael J. Musella, Esq.

(57) ABSTRACT

An OLED encapsulation package, a display device and a packaging method are disclosed. The OLED encapsulation package includes a substrate, a cover board and a encapsulation unit located between the substrate and the cover board; the substrate is provided with display components thereon, and the encapsulation unit encapsulates the periphery of the display components; the encapsulation unit includes at least a moisture sensitive layer therein, and the moisture sensitive layer is capable of discoloring upon encountering with water.

18 Claims, 2 Drawing Sheets

(51) Int. Cl.
*H01L 51/52* (2006.01)
*H01L 51/56* (2006.01)
*G01N 31/22* (2006.01)

(56) References Cited

FOREIGN PATENT DOCUMENTS

| | | |
|---|---:|---|
| CN | 102354695 A | 2/2012 |
| CN | 102468323 A | 5/2012 |
| CN | 102484682 A | 5/2012 |
| CN | 103531719 A | 1/2014 |
| CN | 103730071 A | 4/2014 |
| JP | 2002158088 A | 5/2002 |
| TW | 515062 B | 12/2002 |

OTHER PUBLICATIONS

First Chinese Office Action dated Mar. 1, 2017.
Chinese Office Action dated Mar. 1, 2017.
Second Chinese Office Action dated Aug. 25, 2017.

* cited by examiner

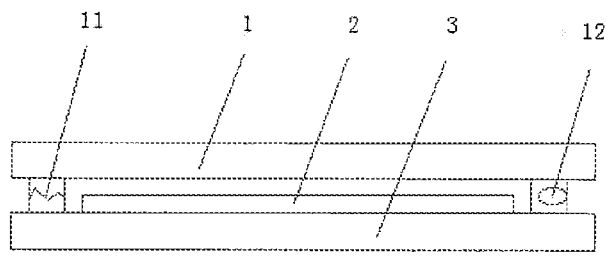
FIG. 1 —Prior Art—
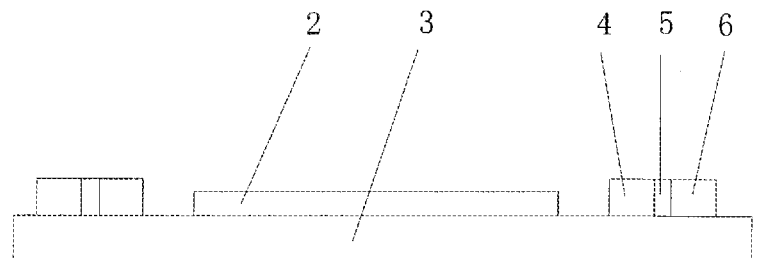
FIG. 2
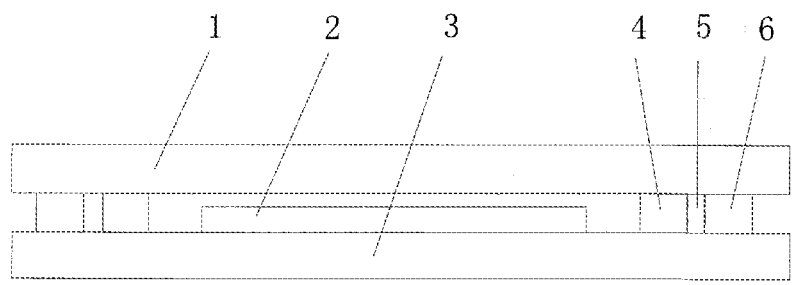
FIG. 3

ENCAPSULATION PACKAGE, DISPLAY DEVICE AND PACKAGING METHOD

TECHNICAL FIELD

The embodiment of present disclosure relates to an organic light emitting diode (OLED) encapsulation package, a display device and a packaging method.

BACKGROUND

OLED is a type of display lighting technology gradually developed in recent years, and especially in the display industry, OLED is regarded as having a comprehensive application prospects due to its advantages, such as being highly responsive, high contrast, flexibility etc.

SUMMARY

Embodiments of the present disclosure provide an organic light emitting diode (OLED) encapsulation package, comprising: a substrate, a cover board and a encapsulation unit located between the substrate and the cover board; the substrate is provided with display components thereon, and the encapsulation unit encapsulates the periphery of the display components; the encapsulation unit at least comprises a moisture sensitive layer therein, and the moisture sensitive layer is capable of discoloring upon encountering with water.

In an embodiment of the present disclosure, for example, the encapsulation unit comprises a first sealing layer, a moisture sensitive layer and a second sealing layer; the first sealing layer, the moisture sensitive layer and the second sealing layer are sequentially disposed from outside to inside on the periphery of the display components.

In an embodiment of the present disclosure, for example, the encapsulation unit comprises a first sealing layer, a moisture sensitive layer and a third sealing layer; the first sealing layer is disposed on the periphery of the display components; the third sealing layer is disposed above the display components and is filled in a space between the substrate and the cover board; the moisture sensitive layer is disposed between the first sealing layer and the third sealing layer.

In an embodiment of the present disclosure, for example, the encapsulation unit comprises a first sealing layer, a moisture sensitive layer, a second sealing layer and a third sealing layer; the first sealing layer, the moisture sensitive layer and the second sealing layer are sequentially disposed from outside to inside on the periphery of the display components; the third sealing layer is disposed above the display components and is filled in a space between the substrate and the cover board; the moisture sensitive layer is disposed between the first sealing layer and the second sealing layer, and/or, between the second sealing layer and the third sealing layer.

In an embodiment of the present disclosure, for example, the first sealing layer is glass adhesive having a coating width from 1 mm to 2 mm and a coating thickness from 10 μm to 100 μm; the second sealing layer is resin adhesive having a coating width from 0.5 mm to 1 mm and a coating thickness from 10 μm to 100 μm.

In an embodiment of the present disclosure, for example, the second sealing layer contains desiccant therein.

In an embodiment of the present disclosure, for example, a gap is provided between the first sealing layer and the second sealing layer for accommodating the moisture sensitive layer, the gap having a width from 0.2 mm to 1 mm.

In an embodiment of the present disclosure, for example, the moisture sensitive layer is a water-absorbing discoloration agent comprising one or more of CaO or $CuSO_4$.

In an embodiment of the present disclosure, for example, the first sealing layer is made of highly viscous sealing material having a viscosity greater than 100000 mPa·s/25° C.; the moisture sensitive layer and the third sealing layer are made of low viscosity sealing material having a viscosity less than 5000 mPa·s/25° C.

In an embodiment of the present disclosure, for example, the substrate is provided with a passivation layer thereon, and the moisture sensitive layer is hermetically connected with the passivation layer through a concave-convex structure.

In an embodiment of the present disclosure, for example, the moisture sensitive layer is doped with one or more of CaO or $CuSO_4$ in a doping concentration from 0.05 wt % to 30 wt %.

Embodiments of the present disclosure provide a display device comprising the above OLED encapsulation package.

Embodiments of the present disclosure provide a method for testing a encapsulation package of an OLED device, comprising: providing a moisture sensitive layer in the encapsulation unit of the encapsulation package of the OLED device, and testing the validity of the encapsulation package of the OLED device by observing the discoloration of the moisture sensitive layer; wherein, if the moisture sensitive layer discolors, it is determined that the interior of the encapsulation unit is subjected to moisture intrusion; and if the moisture sensitive layer does not discolor, it is determined that the interior of the encapsulation unit is in a normal condition.

In an embodiment of the present disclosure, for example, after the determination of the interior of the encapsulation unit being subjected to moisture intrusion, further comprising: temporarily blocking the intruded aqueous and oxygen by the moisture sensitive layer, and patching an adhesive for restoration at a position corresponding to the discoloring site.

BRIEF DESCRIPTION OF THE DRAWINGS

In order to clearly illustrate the technical solution of the embodiments of the disclosure, the drawings of the embodiments will be briefly described in the following; it is obvious that the described drawings are only related to some embodiments of the disclosure and thus are not limitative of the disclosure.

FIG. 1 is a structural schematic view of a conventional OLED device;

FIG. 2 is a schematic view of an OLED encapsulation package of the first embodiment of the present disclosure with the cover board removed;

FIG. 3 is a schematic view illustrating the overall structure of an OLED encapsulation package of the first embodiment of the present disclosure;

Figure 4:
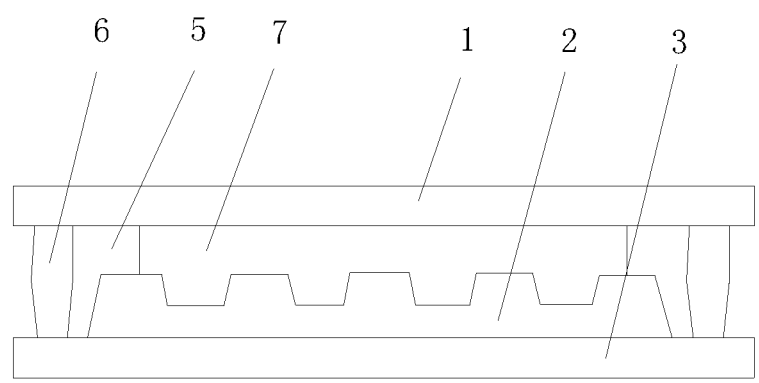
FIG. 4 is a schematic view illustrating the overall structure of an OLED encapsulation package of the second embodiment of present disclosure.

Reference Number: 1: cover board; 2: display components; 3: substrate; 4: second sealing layer; 5: moisture sensitive layer; 6: first sealing layer; 7: third sealing layer; 11: crack; 12: bubble.

DETAILED DESCRIPTION

In order to make objects, technical details and advantages of the embodiments of the disclosure apparent, the technical solutions of the embodiment will be described in a clearly and fully understandable way in connection with the drawings related to the embodiments of the disclosure. It is obvious that the described embodiments are just a part but not all of the embodiments of the disclosure. Based on the described embodiments herein, those skilled in the art can obtain other embodiment(s), without any inventive work, which should be within the scope of the disclosure.

Unless otherwise defined, all the technical and scientific terms used herein have the same meanings as commonly understood by one of ordinary skill in the art to which the present disclosure belongs. The terms "first," "second," etc., which are used in the description and the claims of the present application for disclosure, are not intended to indicate any sequence, amount or importance, but distinguish various components. Also, the terms such as "a," "an," etc., are not intended to limit the amount, but indicate the existence of at least one. The phrases "connect", "connected", etc., are not intended to define a physical connection or mechanical connection, but may include an electrical connection, directly or indirectly.

Because an OLED device would suffer from corrosion damage under the influence of moisture and oxygen, it is particularly important to select a better encapsulation means for the OLED device. The presently widely used encapsulation means comprise adhesive sheet encapsulation, glass adhesive encapsulation or cofferdam filled adhesive encapsulation and the like.

Among these approaches, the glass adhesive package is such a approach in which glass adhesive is used to encapsulate the device and then cures afterwards, and which shows several advantages, such as favorable packaging effects, simpler production flow and the like, thus may have application in the manufacture of small and medium size devices. However, the glass adhesive package also has a certain drawbacks. As shown in FIG. 1, bubble 12 would occur during the glass adhesive coating process, leakage point is also likely to be caused after the curing of the adhesive materials, and the stress would cause crack 11, such harmful factors are difficult to perceive and thus would decrease the product yield. Furthermore, because the glass adhesive is transparent and the leakage point is very small, it is always hard to detect the leakage, and the device would have been failed when the leakage point is finally found.

Because the organic EL device is sensitive to external environment, in particular the side intrusion of the moisture would sometimes lead to decay of device lifetime. In the case of cofferdam filled adhesive package, its decay is a slow process that requires placing the device in a high temperature and high humidity environment for a long time to measure the decay. Thus, how to determine whether the moisture has invaded by a simpler method would not only facilitate a proper analysis of the encapsulation package, the material characteristics and the technologies, but also benefit the screening of an even better display at the same time.

Embodiment 1

As shown in FIGS. 2-3, an OLED encapsulation package provided by this embodiment comprises a substrate 3, a cover board 1, and encapsulation units 4, 5, 6 provided between the substrate 3 and the cover board 1; a display component 2 (OLED, TFE etc.) is arranged on the substrate 3, and the encapsulation units package the periphery of the display components 2; moreover, the interior of the encapsulation unit has at least one moisture sensitive layer 5 which would discolor when in contact with water (including moisture). Through observing the discoloration of the moisture sensitive layer 5, it is possible to conveniently determine a moisture intrusion into the encapsulation package of the OLED device, and it is also easy to analysis the encapsulation package of the devices.

It should be noted that, in this embodiment, it only requires to add a moisture sensitive layer 5 (water-absorbing discoloration agent) in the encapsulation units, which would not only benefit a proper analysis of the encapsulation package, material characteristics and technologies, but also facilitate the screening of an even better display device at the same time. As to the form of the encapsulation units, it can be flexibly set according to actual requirements, as will be illustrated hereinafter.

As shown in FIG. 2, the encapsulation units comprise a first sealing layer 6, a moisture sensitive layer 5 and a second sealing layer 4; the first sealing layer 6, the moisture sensitive layer 5 and the second sealing layer 4 are sequentially provided from outside to inside on the periphery of the display components 2. If encapsulation package fails, such as crack or bubble and the like occurs at the first sealing layer 6, this moisture sensitive layer 5 would discolor.

For example, the first sealing layer 6 is provided at the outermost side. For example, the first sealing layer 6 is glass adhesive having a coating width from 1 mm to 2 mm and a coating thickness from 10 μm to 100 μm, for a better packaging effect; the moisture sensitive layer 5 is provided at an intermediate position. For example, the moisture sensitive layer 5 may be a water-absorbing discoloration agent comprising one or more of CaO or $CuSO_4$, which also may be other indicator agents discoloring significantly upon water absorption. The second sealing layer 4 is provided at the innermost side (but outside of the display components 2). For example, the second sealing layer 4 is resin adhesive having a coating width, for example, from 0.5 mm to 1 mm and having a coating thickness, for example, from 10 μm to 100 μm. Where a gap is provided between the first sealing layer 6 and the second sealing layer 4 for accommodating the moisture sensitive layer 5, and a width of the gap is from 0.2 mm to 1 mm for example.

For example, the resin adhesive of the second sealing layer 4 may be a UV-curable type resin adhesive or a thermosetting resin adhesive, comprising a thehomopolymer or copolymer of the following monomers: epoxy, epoxypropylacrylate, glycidyl methacrylate, methyl methacrylate, ethyl methacrylate, n-butyl methacrylate, methacrylate 6,7-epoxy-heptyl acrylate, 2-Hydroxyethyl methacrylate and the like, and melamine formaldehyde resin, unsaturated polyester resin, silicone resin or furan resin etc.

For example, the second sealing layer 4 may also be added with desiccant therein. For example, the desiccant particles, such as CaO, MgO or BaO etc., are added so as to consolidate the packaging effect.

For example, the materials for the cover board 1 of the OLED may be glass, quartz, plastic and the like, and the materials for the substrate 3 of the OLED may be glass, quartz, plastic, metal and the like.

The packaging process of this embodiment may be carried out as follows: first, coating an organic resin packaging adhesive frame (the second sealing layer 4) on the cover board 1 of the OLED; then, coating glass adhesive (the first sealing layer 6) on the periphery of the frame-sealing adhesive; coating water-absorbing discoloration agent (the moisture sensitive layer 5) between the glass adhesive and the frame-sealing adhesive, then press-fitting the cover board 1 and the substrate 3, curing the frame-sealing adhesive and the glass adhesive, and the encapsulation is completed.

After the completion of the encapsulation, the device is placed into a high temperature and high humidity environment (60° C., 90 RH; or 85° C., 85 RH). If package fails, such as crack or bubble and the like occurs at the glass adhesive, the water-absorbing discoloration agent at this site would discolor. At the same time, the frame-sealing adhesive may temporarily blocks the aqueous oxygen, and the product yield can be increased by repairing the glass adhesive at the discoloring site.

Embodiment 2

As shown in FIG. 4, the technical contents of this embodiment 2 identical to those in the embodiment 1 will not be repeated here, and the disclosure of the embodiment 1 also belongs to the disclosure of this embodiment 2. This embodiment 2 differs from the embodiment 1 in that the encapsulation units adopt another structure as described below.

The encapsulation units comprise a first sealing layer 6, a moisture sensitive layer 5 and a third sealing layer 7; wherein the first sealing layer 6 is provided on the periphery of the display components 2; the third sealing layer 7 is provided above the display components 2 and is filled in a space between the substrate 3 and the cover board 1 (area AA between the substrate 3 and the cover board 1, which is an Active Area); the moisture sensitive layer 5 is provided between the first sealing layer 6 and the third sealing layer 7. Other features have been described in detail above, and the description thereof is omitted herein. Such an encapsulation package dopes moisture sensitive materials in the sealant outside of the AA area, therefore, the encapsulation packaging validity can be effectively determined through the discoloring of the moisture sensitive material upon water absorption.

For example, the first sealing layer 6 is made of highly viscous sealing materials, the viscosity thereof is greater than 100000 mPa·s/25° C., a better packaging effect could be achieved. While the moisture sensitive layer 5 and the third sealing layer 7 are made of low viscosity sealing materials, the viscosity thereof is less than 5000 mPa·s/25° C., which could not only realize the packaging, but also satisfy the effect of press-fitting and filling. Undoubtedly, specific materials for each sealing layer are not restricted thereto, but could be provided variably according to actual requirements.

In order to obtain an even better packaging and sealing effect, a passivation layer is provided on the substrate 3, and the moisture sensitive layer 5 is hermetically connected with the passivation layer through a concave-convex structure, thereby obtaining a better sealing effect.

For example, the moisture sensitive layer 5 may be doped with one or more materials of CaO or $CuSO_4$, however, the materials are not limited to the moisture sensitive materials, such as CaO, $CuSO_4$ and the like, any indicator agent is possible as long as it could discolor significantly upon contacting with water. For example, these moisture sensitive materials have a doping concentration from 0.05 wt % to 30 wt %. Through observing the discoloration of the moisture sensitive layer 5, it is possible to conveniently determine a moisture intrusion into the encapsulation package of the OLED device, and it is also easy to analysis the encapsulation package of the devices.

Embodiment 3

This embodiment 3 provides further variation on the basis of the embodiments 1 and 2. The encapsulation units comprise a first sealing layer 6, a moisture sensitive layer 5, a second sealing layer 4 and a third sealing layer 7, the first sealing layer 6, the moisture sensitive layer 5 and the second sealing layer 4 are provided from outside to inside on the periphery of the display components 2; the third sealing layer 7 is provided above the display components 2 and is filled in a space between the substrate 3 and the cover board 1. It is thus evident that, in this embodiment, it is also possible to determine the packaging effect of the OLED by bereaving the discoloration situation in the moisture sensitive layer 5 employing such a four-layered encapsulation package.

To be specified, there is no limitation on the number of each of the sealing layers in the above encapsulation unit, but could be provided flexibly according to actual requirements as long as the moisture sensitive layer 5 is included.

Embodiment 4

Embodiment 4 provides a display device comprising the above OLED encapsulation package. The OLED encapsulation package comprises a substrate 3, a cover board 1 and encapsulation units located between the substrate 3 and the cover board 1; display components 2 are provided on the substrate 3, the encapsulation units are disposed on the periphery of the display components 2; moreover, the interior of the encapsulation units comprise at least one moisture sensitive layer 5 which could discolor upon contacting with water. Through observing the discoloration of the moisture sensitive layer 5, it is possible to conveniently determine a moisture intrusion into the encapsulation package of the OLED device, and it is also easy to analysis the encapsulation package of the devices. Other features have been described in detail above, and the description thereof is omitted herein.

Embodiment 5

Embodiment 5 provides a method for testing the encapsulation package of an OLED device, the method comprises: providing a moisture sensitive layer 5 in the encapsulation units of the encapsulation package of the OLED device, and testing the validity of the encapsulation package of the OLED device by observing the discoloration of the moisture sensitive layer 5; wherein, if the moisture sensitive layer 5 discolors, it is determined that the interior of the encapsulation unit is subjected to moisture intrusion; and if the moisture sensitive layer 5 does not discolor, it is determined that the interior of the encapsulation unit is in a normal condition.

For example, after the determination of the interior of the encapsulation unit being subjected to moisture intrusion, the method further comprises: temporarily blocking the intruded aqueous and oxygen by the moisture sensitive layer 5, and patching an adhesive for restoration at the position corresponding to the discoloring site.

For example, the packaging, detecting and repairing processes comprise: making a layer of UV-light curable type organic resin frame-sealing adhesive layer (the second sealing layer 4), on the glass cover board, having a height of 20 μm, a width of 1 mm and doped with desiccant, coating glass adhesive (the first sealing layer 6) of a width of 1 mm, a height of 20 μm at an area spaced apart from the periphery of the frame-sealing adhesive by 0.5 mm; coating CaO powder between the frame-sealing adhesive and the glass adhesive, aligning and press-fitting the OLED substrate 3 and the cover board 1, curing the frame-sealing adhesive and the glass adhesive by UV-irradiation, thus completing the encapsulation. The resultant packaged device is put into an environment of 85° C., 85 RH for 50 h, then it is taken out to observe discoloration of the water-absorbing discoloration agent, if the water-absorbing discoloration agent does not discolor, the product is in normal state; if there is a discoloration, then patching adhesive for restoration is performed to the glass adhesive at the discoloring site, the frame-sealing adhesive could protect the devices under a high temperature and high humidity environment from moisture intrusion.

The above are only the model implementation ways of the present disclosure, and not used to limit the scope of protection of the present disclosure, the scope of protection of the present disclosure is determined by the attached claims.

The present application claims the priority of the Chinese Patent Application No. 201610052797.9 filed on Jan. 26, 2016, which is incorporated herein by reference as part of the disclosure of the present application.

What is claimed is:

1. An organic light emitting diode (OLED) encapsulation package, comprising:
a substrate, a cover board and a encapsulation unit located between the substrate and the cover board;
wherein the substrate is provided with display components thereon, and the encapsulation unit encapsulates periphery of the display components;
the encapsulation unit at least comprises a moisture sensitive layer therein, and the moisture sensitive layer is capable of discoloring upon encountering with water;
wherein the encapsulation unit comprises a first sealing layer, the moisture sensitive layer and a second sealing layer; and
the first sealing layer, the moisture sensitive layer and the second sealing layer are sequentially disposed from outside to inside on the periphery of the display components.

2. The OLED encapsulation package according to claim 1, wherein the encapsulation unit comprises a first sealing layer, the moisture sensitive layer and a third sealing layer;
the first sealing layer is disposed on the periphery of the display components;
the third sealing layer is disposed above the display components and is filled in a space between the substrate and the cover board; and
the moisture sensitive layer is disposed between the first sealing layer and the third sealing layer.

3. The OLED encapsulation package according to claim 1, wherein the encapsulation unit comprises a first sealing layer, the moisture sensitive layer, a second sealing layer and a third sealing layer;
the first sealing layer, the moisture sensitive layer and the second sealing layer are sequentially disposed from outside to inside on the periphery of the display components;
the third sealing layer is disposed above the display components and is filled in a space between the substrate and the cover board; and
the moisture sensitive layer is disposed between the first sealing layer and the second sealing layer, and/or disposed between the second sealing layer and the third sealing layer.

4. The OLED encapsulation package according to claim 1, wherein the first sealing layer is glass adhesive having a coating width from 1 mm to 2 mm and a coating thickness from 10 im to 100 im;
the second sealing layer is resin adhesive having a coating width from 0.5 mm to 1 mm and a coating thickness from 10 im to 100 im.

5. The OLED encapsulation package according to claim 1, wherein the second sealing layer contains desiccant therein.

6. The OLED encapsulation package according to claim 1, wherein a gap is provided between the first sealing layer and the second sealing layer for accommodating the moisture sensitive layer, and the gap having a width from 0.2 mm to 1 mm.

7. The OLED encapsulation package according to claim 1, wherein the moisture sensitive layer is a water-absorbing discoloration agent comprising one or more of CaO or $CuSO_4$.

8. A display device comprising the OLED encapsulation package according to claim 1.

9. The OLED encapsulation package according to claim 2, wherein the first sealing layer is made of a viscous sealing material having a viscosity greater than 100000 mPa·s/25° C.;
the moisture sensitive layer and the third sealing layer are made of a viscosity sealing material having a viscosity less than 5000 mPa·s/25° C.

10. The OLED encapsulation package according to claim 2, wherein the substrate is provided with a passivation layer thereon, and the moisture sensitive layer is hermetically connected with the passivation layer through a concave-convex structure.

11. The OLED encapsulation package according to claim 2, wherein the moisture sensitive layer is doped with one or more of CaO or $CuSO_4$ in a doping concentration from 0.05 wt % to 30 wt %.

12. The OLED encapsulation package according to claim 3, wherein the first sealing layer is glass adhesive having a coating width from 1 mm to 2 mm and a coating thickness from 10 im to 100 im; and
the second sealing layer is resin adhesive having a coating width from 0.5 mm to 1 mm and a coating thickness from 10im to 100 im.

13. The OLED encapsulation package according to claim 3, wherein the second sealing layer contains desiccant therein.

14. The OLED encapsulation package according to claim 3, wherein a gap is provided between the first sealing layer and the second sealing layer for accommodating the moisture sensitive layer, and the gap having a width from 0.2 mm to 1 mm.

15. The OLED encapsulation package according to claim 3, wherein the moisture sensitive layer is a water-absorbing discoloration agent comprising one or more of CaO or $CuSO_4$.

16. The OLED encapsulation package according to claim 3, wherein the first sealing layer is made of a viscous sealing material having a viscosity greater than 100000 mPa·s/25° C.; and
the moisture sensitive layer and the third sealing layer are made of a viscosity sealing material having a viscosity less than 5000 mPa·s/25° C.

17. The OLED encapsulation package according to claim 3, wherein the substrate is provided with a passivation layer thereon, and the moisture sensitive layer is hermetically connected with the passivation layer through a concave-convex structure.

18. A method for testing an encapsulation package of an organic light emitting diode (OLED) device, comprising:
providing a moisture sensitive layer in an encapsulation unit of the encapsulation package of the OLED device, and
testing validity of the encapsulation package of the OLED device by observing discoloration of the moisture sensitive layer; wherein
if the moisture sensitive layer discolors, it is determined that interior of the encapsulation unit is subjected to moisture intrusion, temporarily blocking intruded aqueous and oxygen by the moisture sensitive layer, and patching an adhesive for restoration at a position corresponding to the discoloring site; and if the moisture sensitive layer does not discolor, it is determined that the interior of the encapsulation unit is in a normal condition.

\* \* \* \* \*